United States Patent
Schmidt et al.

(10) Patent No.: US 6,252,073 B1
(45) Date of Patent: Jun. 26, 2001

(54) METHOD OF PRODUCING ALKALI METAL SALTS OR ALKALINE EARTH METAL SALTS OF 2,4-DICHLORO-6-HYDROXY-S-TRIAZINE

(75) Inventors: Manfred Schmidt, Geinhausen; Christoph Klatte, Gründau; Kurt Kunz, Birstain; Josef Leutner, Grossheubach; Jürgen Ohlemacher, Maintal; Hans Peter Krimmer, Dietzenbach, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/369,459

(22) Filed: Aug. 6, 1999

(30) Foreign Application Priority Data

Aug. 7, 1998 (DE) .............................. 198 35 774

(51) Int. Cl.⁷ .................................. C07D 251/26
(52) U.S. Cl. ............................ 544/190; 544/216
(58) Field of Search ..................... 544/190, 216

(56) References Cited

FOREIGN PATENT DOCUMENTS

| 115 121 | 9/1975 | (DE) . |
|---|---|---|
| 29 10 726 | 10/1979 | (DE) . |
| 44 24 733 A1 | 1/1995 | (DE) . |
| 0 597 312 A1 | 5/1994 | (EP) . |
| 0 616 071 A1 | 9/1994 | (EP) . |
| 59-106474 | 6/1984 | (JP) . |
| 1 051 082 | 10/1983 | (SU) . |

OTHER PUBLICATIONS

Smolin & Rapoport, Cyanuric Acid & Derivatives, Chp. 1 (1967), pp. 53–54.

*Primary Examiner*—John M. Ford
*Assistant Examiner*—Venkataraman Balasubramanian
(74) *Attorney, Agent, or Firm*—Pillsbury Winthrop LLP

(57) ABSTRACT

A method for producing alkali metal salts or alkaline earth metal salts of 2,4-dicloro-6-hydroxy-s-triazine, especially the sodium salt, by reacting cyanuric chloride with an alkali hydroxide or alkaline earth hydroxide. 1 to 2.5 Equivalents of alkali hydroxide or alkaline earth hydroxide per mole cyanuric chloride in the form of an aqueous solution or suspension are placed in a receiver and cyanuric chloride in powder form or in the form of an aqueous suspension is added while maintaining a pH in the range of 9.5 to 14 and cooling. If less than a stoichiometric amount is added to the receiver, the remaining amount of alkali hydroxide or alkaline earth hydroxide is added during and/or after the addition of cyanide chloride, while maintaining the pH. The method can be carried out on an industrial scale and formation of the salt of monochlorodihydroxytriazine is largely avoided.

5 Claims, No Drawings

METHOD OF PRODUCING ALKALI METAL SALTS OR ALKALINE EARTH METAL SALTS OF 2,4-DICHLORO-6-HYDROXY-S-TRIAZINE

CROSS-REFERENCE TO RELATED APPLICATION

This application is based on German Application DE 198 35 774.5, filed Aug. 7, 1998, which disclosure is incorporated herein by reference.

FIELD OF THE INVENTION

The invention relates to a method for producing alkali metal salts or alkaline earth metal salts of 2,4-dicloro-6-hydroxy-s-triazine, especially the sodium salt (DCHT-Na), by reacting cyanuric chloride with an alkali hydroxide or alkaline earth hydroxide. The method can be operated on an industrial scale.

BACKGROUND OF THE INVENTION

Alkali metal salts of 2,4-dichloro-6-hydroxy-s-triazine are used as raw material for reactive dyes, as cross-linking agents for photo gelatins and recently as formaldehyde-free cross-linking agents for producing wrinkle-proof and easy-care properties of fibrous materials containing cellulose—see EP-A 0,616,071. Due to the decomposable nature of the solid triazine derivative the latter is usually not isolated but rather processed further in an aqueous phase.

It is known that cyanuric chloride can be hydrolyzed with alkali hydroxides to 2,4-dichloro-6-hydroxy-s-triazine and 2-chloro-4,6-dihydroxy-s-triazine—see Smolin and Rappoport, The Chemistry of Heterocyclic Compounds, S-Triazines and Derivatives (1967), 53–54. According to this document the hydrolysis does not stop at the desired first stage but rather the second and third chlorine atom are hydrolyzed at least partially in some instances.

According to German Patent DD 115 121, the 2,4-dichloro-6-hydroxy-s-triazine-Na salt, abbreviated in the following as DCHT-Na, is produced by the addition of cyanuric chloride dissolved in benzene or chloroform to an aqueous solution of sodium carbonate or sodium bicarbonate at 15° C. The use of organic solvents and the development of $CO_2$ from $Na_2CO_3$ or $NaHCO_3$ are disadvantageous. In the method according to JP-A 59-106474, 2.0 to 2.6 mol $NaHCO_3$ are added in the hydrolysis per mole cyanuric chloride together with a buffer, e.g., a phosphate buffer.

If cyanuric chloride is to be converted into DCHT-Na by sodium hydroxide solution instead of by sodium bicarbonate, according to SU-A 1051082, a buffer is again used and the reaction carried out at pH 8.5 to 8.8. However, the buffer is frequently undesirable since the solution is processed further. In addition, there is the risk of the pH dropping to values below 7 in this method of operation on account of the limited buffer capacity and thus an increased formation of the di- and trihydroxytriazine derivatives.

K. Matsui and J. Sakomoto show in Yuki Gosei Kagaku 18 (1960), H.3, 175–183 (45–53) that for the production of 2,4-dichloro-6-hydroxy-s-triazine (DCHT-Na) sodium hydroxide solution should be added at 0 to 5° C. to a suspension of cyanuric chloride. On the other hand, for the production of 2-chloro-4,6-dihydroxytriazine-Na salt (CDHT-Na) a cyanuric chloride suspension is charged into a sodium hydroxide solution. It was found during the reworking of the method described in this document that DCHT-Na can be produced in this way on a laboratory scale, but that this method poses safety problems on an industrial scale. Reaction heat is released which is difficult to control or, alternatively, the reaction rate is too slow.

SUMMARY OF THE INVENTION

An object of the invention is to optimize the hydrolysis of cyanuric chloride to DCHT-Na using sodium hydroxide solution in such a manner that the reaction remains reliably controllable even on an industrial scale.

The problem is solved by a method of producing an alkali metal salt or an alkaline earth metal salt of 2,4-dicloro-6-hydroxy-s-triazine by hydrolyzing cyanuric chloride with aqueous alkali hydroxide or alkaline earth hydroxide at a temperature equal to or below 10° C. 1 to 2.5 Equivalents of alkali hydroxide or alkaline earth hydroxide per mole cyanuric chloride in the form of an aqueous solution or suspension are placed in a receiver and cyanuric chloride in powder form or in the form of an aqueous suspension is added thereto while maintaining the pH in the range of 9.5 to 14 and cooling. In the case of a less than stoichiometric amount of alkali hydroxide or alkaline earth hydroxide being used, the remaining amount, including an excess of up to 25%, is added during and/or after the addition of cyanuric chloride for the purpose of maintaining the pH. The reaction is terminated when the pH essentially no longer changes at the temperature selected.

It has surprisingly been found that, in the method of the invention, cyanuric chloride can be hydrolyzed with high selectivity to the corresponding DCHT salt in spite of an excess of alkali hydroxide or alkaline earth hydroxide in the receiver. Only a small quantity of the 2-chloro-4,6-dihydroxy-s-triazine salt is formed. The method can also be safely operated on an industrial scale because the heat of reaction can be reliably removed or controlled and the pH maintained preferably above 10. A batch operation in accordance with the invention can be carried out at least partially and can also be followed by a continuous method of operation: In this case a suspension of cyanuric chloride and an alkali lye or a suspension of alkaline earth hydroxide are added in an approximately stoichiometric ratio into the reaction mixture of the batch. At the same time, and under cooling and monitoring of the pH, an amount corresponding to the amount added is drawn off from the reactor, which is advantageously designed as a circulation reactor, and the latter amount maintained at reaction temperature in a reactor connected at the outlet side, e.g., a tubular reactor, until the end of the reaction.

The alkaline metal salts to be produced in accordance with the invention are in particular, the Li—, Na—or K— salts. The alkaline earth metal salts are, in particular, the Mg—, Ca— Sr— or Ba— salts. The Na salt is particularly preferred. The concentration of the alkali hydroxide solution or alkaline earth hydroxide solution is adjusted according to the final concentration of DCHT-Na that is desired. Cooling may take place by direct cooling with ice or by indirect cooling. For a more rapid reaction, a wetting agent can be added to the alkali lye or suspension of alkaline earth hydroxide or suspension of cyanuric chloride placed in the receiver. A more rapid addition of cyanuric chloride makes faster removal of heat necessary.

Even though the theoretical molar ratio of alkali hydroxide to cyanuric chloride is 2 to 1, it can be advantageous to add alkali hydroxide in an excess of up to 25%, preferably in an excess up to 10%, during the last phase of the reaction, that is, after the end of the addition of cyanuric chloride, in order to maintain the pH and stabilize the reaction mixture.

According to a preferred embodiment, alkali hydroxide is placed in the receiver in an amount of 1.2 to 2.2 moles, preferably 1.5 to 2.0 moles, per mole cyanuric chloride. When alkaline earth hydroxides are used the previously cited molar ratio corresponds to the equivalent ratio.

It is important to maintain the pH at values above 9.5, preferably above 10, during the addition of cyanuric chloride and during the postreaction period. The final pH should preferably be in a range of 10 to 12. At a pH below 9.5 there is a danger that the pH will drop into the acidic range with a consequent increased formation of salts of dihydroxy-monochlorotriazine (CDHT) and cyanuric acid. The reaction is usually carried out at a temperature in the range of $-10°$ to $+10°$ C., preferably $-5°$ to $+5°$ C., and more preferably at 0 to 3° C.

The method can be reliably managed and operated with a high space-time yield. The DCHT salt obtained contains only a very small amount of the undesirable byproduct CDHT salt.

DETAILED DESCRIPTION OF THE PREFERRED EMBODIMENTS

Example 1

20 kg cyanuric chloride were suspended in approximately 47 kg water in a thermostatically controlled 100 liter enamel container and cooled to approximately 0° C. 50 liters water, 60 kg ice and 15 kg 50% NaOH were placed into a 500 liter receiver with an agitator. The temperature of the mixture dropped to approximately $-8°$ C.

A suspension of cyanuric chloride was pumped at intervals out of the 100 liter container into the receiver. The temperature rose slowly and was maintained at a maximum of $+2°$ C. by gradually adding portions of ice (a total of 120 kg for the entire reaction time). Toward the end of the dosing, the pH began to drop and the pH was maintained between 10 and 11 by the addition of 2 kg 50% by weight NaOH solution. The reaction was terminated, as shown by HPLC analysis (column: 2×Lichrospher 100 RP 18 (5 $\mu$m from Merck)), when the pH no longer changed at constant temperature. The dosing of the suspension lasted ¾ hour and the total reaction required approximately 3 hours. HPLC analysis of the reaction mixture after the end of the reaction showed that cyanuric chloride was converted into 99.7% 2,4-dichloro-6-hydroxy-s-triazine-Na salt (DCHT-Na salt), 0.2% 2-chloro-4,6-dihydroxy-s-triazine-Na salt (CDHT—Na salt) and 0.1% Na salt of cyanuric acid.

Example 2

20 kg cyanuric chloride were reacted with a total of 16.4 kg 50% by weight sodium hydroxide solution: A mixture of 50 kg water, 10 kg sodium hydroxide solution (50% by weight) and 60 kg ice were placed in a receiver. The temperature of the mixture was $-5°$ C. An aqueous suspension of 20 kg cyanuric chloride and 50 kg water, which suspension had previously been cooled down to 0° C., was added within 45 minutes under intensive agitation and cooling by the addition of ice (a total of approximately 120 kg) and the pH maintained to the extent required at pH values in a range of 10 to 14 by the addition of sodium hydroxide solution. The temperature was maintained during the addition of cyanuric chloride (approximately 1 hour) and during the subsequent addition of the remaining amount of sodium hydroxide solution at 0 to 1° C. in order to maintain a pH of 10 to 14. After 3.5 hours when the reaction was terminated, the pH was 10.5.

HPLC analysis (surface %): 99.4% DCHT-Na salt, 0.5% CDHT—Na salt and 0.1% cyanuric acid Na salt.

Example 3

Example 2 was repeated; however, the pH dropped briefly to below 10 and the temperature was elevated after 1.5 hours from 0 to 1° C. up to 3° C. The reaction was terminated after 2.5 hours. HPLC analysis: 96.6% DCHT-Na salt, 3.2% CDHT-Na salt, 0.1% cyanuric acid Na salt.

What is claimed is:

1. A method of producing an alkali metal salt or alkaline earth metal salt of 2,4-dichloro-6-hydroxy-s-triazine, by hydrolyzing cyanuric chloride with aqueous alkali hydroxide or alkaline earth hydroxide at a temperature of $-5°$ to $+5°$ C., comprising:

placing in a receiver 1 to 2.5 equivalents alkali hydroxide or alkaline earth hydroxide per mole cyanuric chloride in the form of an aqueous solution or suspension;

adding cyanuric chloride in powder form or in the form of an aqueous suspension into the receiver while maintaining a pH of at least 10;

cooling the contents of the receiver and maintaining a temperature in a range of $-5°$ to $+5°$ C.;

if less than a stoichiometric amount of alkali hydroxide or alkaline earth hydroxide was added, adding the remaining amount including a stoichiometric excess of up to 25% into the receiver during and/or after the addition of cyanuric chloride for the purpose of maintaining the pH, and terminating the reaction when the pH substantially no longer changes at the temperature selected.

2. The method according to claim 1, wherein the 2,4-dichloro-6-hydroxy-striazine Na salt is produced using sodium hydroxide solution as the alkali hydroxide solution.

3. The method according to claim 2, wherein 1.2 to 2.2 moles sodium hydroxide per mole cyanuric chloride is placed in the receiver and cyanuric chloride is added in the form of an aqueous suspension.

4. The method according to claim 3, wherein 1.5 to 2.2 moles of sodium hydroxide per mole cyanuric chloride is used.

5. The method according to claim 1, wherein the temperature is maintained in a range of 0 to 3° C.

* * * * *